United States Patent [19]

Morgan

[11] Patent Number: 4,917,701
[45] Date of Patent: Apr. 17, 1990

[54] TEMPOROMANDIBULAR JOINT PROSTHESES

[76] Inventor: Douglas H. Morgan, 3043 Foothill Blvd., La Crescenta, Calif. 91214

[21] Appl. No.: 242,524

[22] Filed: Sep. 12, 1988

[51] Int. Cl.[4] .............................................. A61F 2/28
[52] U.S. Cl. ........................................ 623/16; 623/18
[58] Field of Search .................................... 623/16, 18

[56] References Cited

U.S. PATENT DOCUMENTS

| 4,726,808 | 2/1988 | Collins | 623/16 |
| 4,778,472 | 10/1988 | Homsy et al. | 623/18 |

FOREIGN PATENT DOCUMENTS 1332071 10/1973 United Kingdom .................. 623/18

*Primary Examiner*—Alan W. Cannon
*Assistant Examiner*—N. Paul
*Attorney, Agent, or Firm*—Don Lawrence

[57] ABSTRACT

A total TMJ replacement system comprises a temporal implant component and a mandibular implant component.

The temporal component comprises a thin, rigid plate of Vitallium ® which is contoured to generally conform to and overlay at least the articular eminence and mandibular fossa portions of the glenoid fossa, but not the petro-tympanic fissure. A layer of Silastic ® is securely attached to the superior surface of the plate and is disposed to reside between the plate and the floor of the mandibular fossa to act as both a filler and a means for adjusting the vertical position of the plate relative to the floor of the natural fossa. The plate includes a lateral flange which is screwed to the zygion to hold the plate securely in place.

A preferred form of the mandibular component comprises a rigid, thin-walled, generally upright channel having a J-shaped cross-section with open upper and lower ends, which is formed of Vitallium, to slip over and generally conform to the posterior border of a natural ramus from which the condyle has been removed. The channel is secured to the ramus with screws. An artificial condyle, comprising an anatomically-correct, laterally elongated and tapered head disposed above a narrowed neck and shoulders, is molded onto the upper end of the channel from a hard, smooth, acrylic such that it fairs smoothly onto, and serves as a closure for, the upper end of the channel.

19 Claims, 2 Drawing Sheets

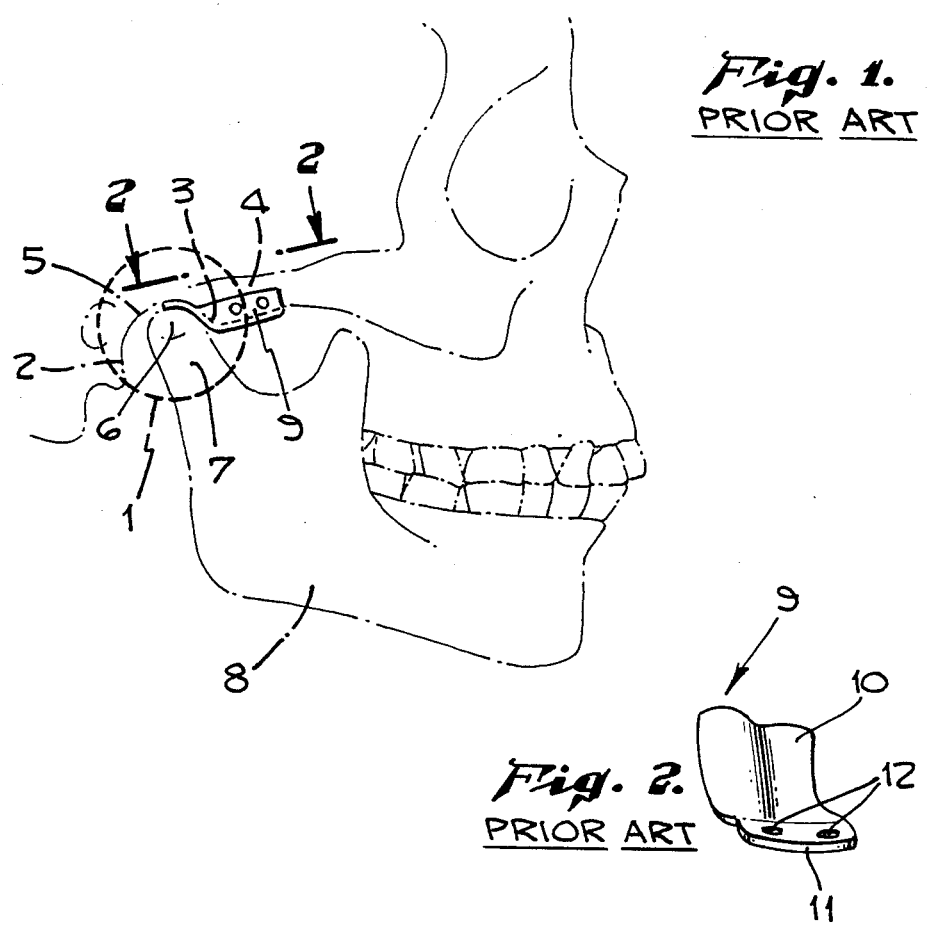
*Fig. 1.*
PRIOR ART
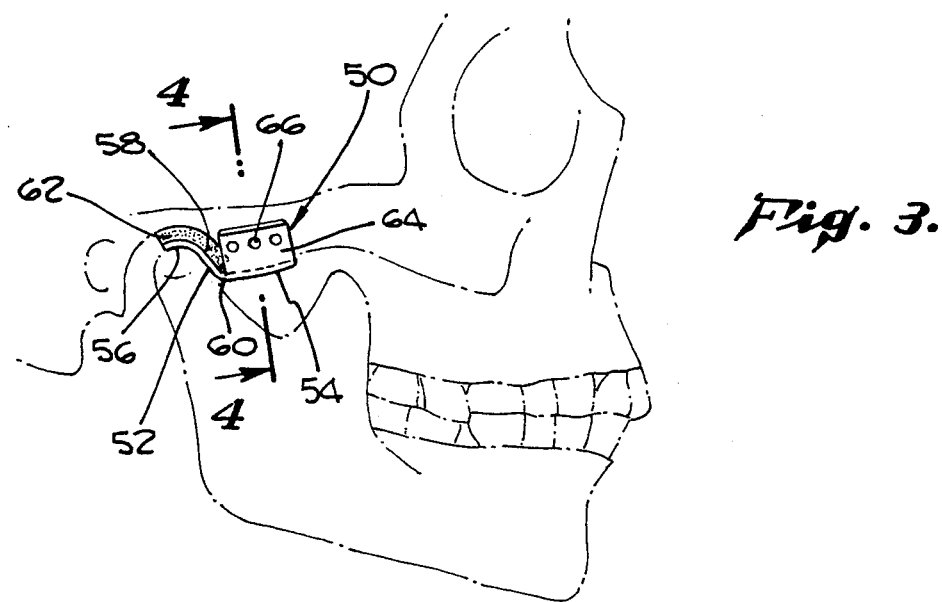
*Fig. 2.*
PRIOR ART
*Fig. 3.*

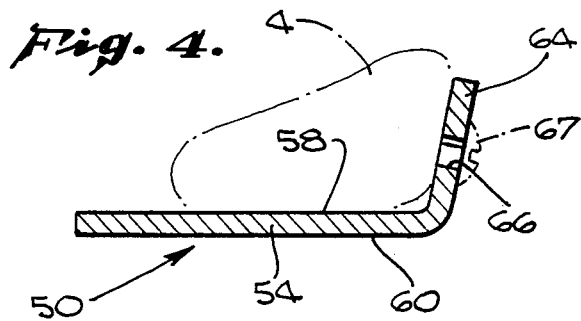
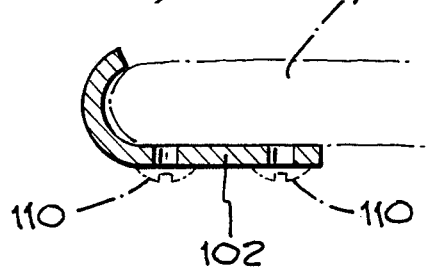
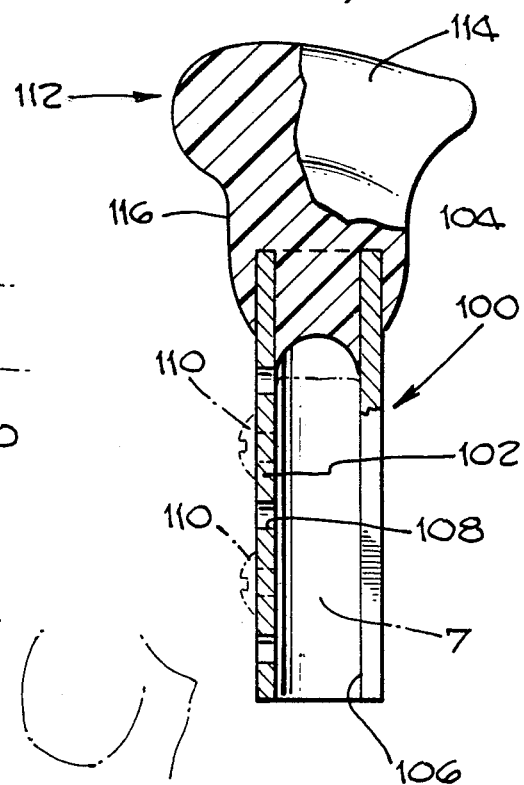
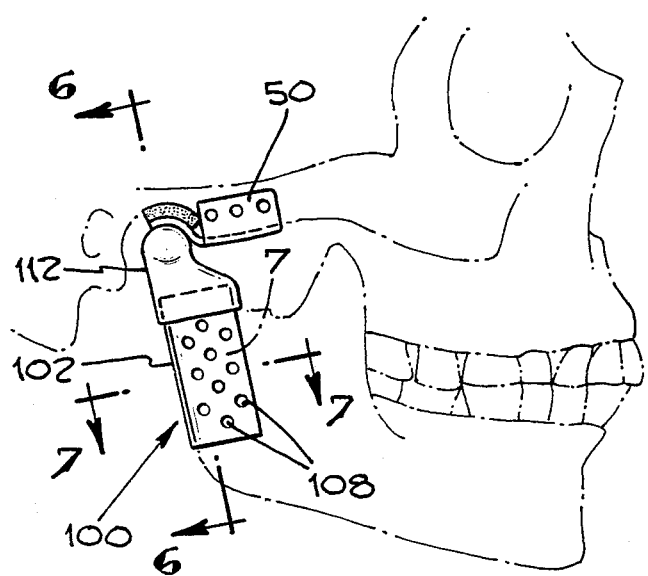

TEMPOROMANDIBULAR JOINT PROSTHESES

BACKGROUND OF THE INVENTION

1. Field of the Invention

This invention relates to surgicomedical prostheses in general, and in particular, to a total temporomandibular joint replacement system, including a temporal implant and a mandibular implant.

2. Description of the Related Art

Disease of the temporomandibular joint (TMJ) is often undiagnosed or misdiagnosed because it mimics many different diseases and has such a wide variety of symptoms.[1]

[1] Morgan, D. H., "The Great Imposter—Diseases of the Temporomandibular Joint;" *JAMA*, vol. 235, p.2395, May, 1976.

Most people who have this problem suffer from a myo-facial pain-dysfunction syndrome primarily as a muscle problem related to dental or skeletal malrelationships and tensional factors, or in some cases, as a reversible irritation in the joint. Most of these patients can be successfully treated using nonsurgical techniques. The remaining individuals usually have organic disease within the joint, usually osteoarthritis, and the latter often require some form of surgical treatment.

Much of the TMJ surgery that has been performed to date has been the result of pathological arthritic changes within the joint, e.g., ankylosis, a bony or fibrous fusion of the condyle (ball) to the mandibular fossa (socket). The surgical technique most commonly employed for treatment of this condition is essentially a form of osteoarthrotomy. Other surgical techniques, variously favored for symptoms other than ankylosis, include condylectomy, high condylelctomy, condylotomy, eminectomy, zygoectomy, meniscectomy, meniscus replacement and/or repair, and placement of various implants.[2]

[2] House, L. R., et al; "Temporomandibular Joint Surgery: Results of a 14-Year Joint Implant Study;" *Laryngoscope*, vol.94, no.4, pp.534–538, Apr., 1984.

For many years, TMJ interpositional arthroplasty has been an accepted surgical modality in the treatment of severe ankylosis. Typically, an osteotomy is performed at or below the line of the joint, and this may be accompanied by a partial or total diskectomy. In such procedures, it has been common to utilize some form of implant or prosthesis, either within the fossa or upon the condylar stump, or both, in order to restore approximately correct anatomic interpositional fit, if not function.

In the past, the implantation of metal fossa has been a commonly used technique for treatment of ankylosis. One such type of implant is described by R. W. Christensen in U.S. Pat. No. 3,178,728. This prosthesis is contoured to fit within the glenoid fossa and overlay the articular eminence, and has been successfully employed in a relatively large number of cases.

However, in order to ensure a good fit between the prosthesis and the glenoid fossa, i.e., one which does not disturb the relation of the teeth and bite, it was necessary to provide these implants in up to 60 different sizes for each side, and a considerable amount of time was consumed in fitting them to the joint during surgery.

In U.S. Pat. No. 3,579,643, I disclosed an improvement over the preceding device in the form of a metallic articular eminence implant which was used for conditions other than ankylosis and which covered only the articular eminence of the temporal component of the joint. Since it was not designed to prevent a true bony or fibrous ankylosis from recurring, it was not necessary to cover the mandibular fossa portion of the joint. This permitted the provision of the device in only one size per side, although some surgical shaving of the eminence was occasionally required. Eventually, I found that, by having a variety of about ten sizes per side, the necessity of shaving of the eminences to arrive at a good fit could be reduced further.

The most popular material for interpositional arthroplasty implants has been a form of silicone rubber, e.g., Silastic ®, usually in the form of silicone rubber blocks or Dacron-reinforced sheaths of silicone rubber, primarily because of the material's biomedical compatibility or inertness, and because of its elasticity and the ease with which it can be worked and shaped to fit the anatomy of an individual patient's fossa. J. N. Kent, et al,-[3] describe a form of custom-fitted, laminated construction, glenoid fossa implant having a superior layer consisting of Proplast ®, a middle layer of Nomex ® fabric impregnated with Teflon ® FEP polymer, and an inferior layer of hard-fused Teflon TFE (Syncar ®) polymer reinforced with graphite fiber disposed for articulation with the condyle. A variation of this implant is found in U.S. Pat. No. 248,665.

[3] Kent, J. N., et al; "Temporomandibular Joint Condylar Prosthesis: A Ten-year Report; *J. Oral and Maxillofacial Surgery*, vol. 41, pp. 245–254, 1983.

Unfortunately, silicone rubber materials, when used alone or as a functioning joint, can result in the loss of good biomechanical fit and jaw function caused by long term creep and flow of the material,[4] as well as pathological sequelae in the nature of destructive lesions of the mandibular condyle, in which the material becomes abraided by the passage over it of the rough condylar bone, thereby causing particles of the material to slough off and be dispersed into the surrounding tissue.[5] These particles, unless they become walled off by fibrous connective tissue, can result in a foreign-body giant cell reaction and reactive synovitis.

[4] Kent, J. N., et al, supra, at p. 252.

[5] Westesson, P. L., et al; "Destructive Lesions of the Mandibular Condyle Following Diskectomy with Temporary Silicone Implant;" *Oral Surgery*, pp. 143–150.

In addition to fossa prosthesis, TMJ surgical procedures often include some form of condylar prosthesis, either alone or as part of a total TMJ replacement. An early form of a condylar implant is found in U.S. Pat. No. 248,492, and comprised an all-metal prosthesis cast from a surgical alloy to include a nonanatomic head, a neck portion and a flattened shank portion which was coated with Proplast ® and screwed to the lateral surface of the ramus for fixation. A report on the use of this and a similar type of condylar implant over a ten year period in which 109 prostheses were placed in 80 patients is given by J. N. Kent, et al.[6]

[6] Kent, J. N., et al, supra.

One of the problems with an all metal, non-anatomic condyle is its tendency to wear away the mandibular fossa in which it resides. In this regard, it is to be noted that the mandibular fossa does not normally act as part of the functioning joint, but rather, merely as a "garage" in which the condyle is "parked" when at rest. During functioning, the condyle translates over the "driveway" of the articular eminence. However, after a condylectomy, the attachment of the lateral pterygoid muscle, which translates the condyle over the eminence, is usually lost. A hinging motion of the condyle within the articular eminence then results, leading to a wearing away of the bony fossa by the non-anatomic metallic head, which is unable to spread the forces over the fossa as evenly as a natural condyle would. An instance wherein the head of a metallic condyle actually penetrated through the bony glenoid fossa and into the cranial cavity of a patient with rheumatoid arthritis is reported by J. N. Kent, et et al.[7]

[7] Id., at p. 250.

From the foregoing, it will be seen that a desirable total TMJ replacement system is one that includes a temporal component which combines the stiffness and hard wearing surface of the metallic fossae prostheses with the adjustability and ease of fit of the silicone rubber implants, while avoiding the latter's problems, as well as a condylar component which is as strong and as durable as the metallic prostheses, but which has a head of a softer, more anatomically-shaped material which would not tend to wear away the bony fossae and which spreads the wearing forces more evenly thereon. The present invention discloses a TMJ replacement system which provides these advantages.

SUMMARY OF THE INVENTION

These advantages, and others, are preferably achieved in a total TMJ replacement system comprising a temporal component implant and a mandibular component implant which can be used in conjunction with each other or, if appropriately indicated, independently of one another and in conjunction with their natural complements.

The temporal component comprises a thin, rigid plate of biologically inert material, preferably Vitallium ®, which is contoured to generally conform to and overlay at least the articular eminence and a part of the mandibular fossa portion of an average-sized glenoid fossa.

A layer of resilient, biologically inert material of adjustable thickness, preferably Silastic ®, is securely attached to the superior surface of the plate and is disposed to reside between the plate and the floor of the mandibular fossa, and to act as both a filler and a means for adjusting the vertical position of the plate relative to the floor of a particular patient's fossa. The inferior surface of the plate is smoothly polished and entirely free of the resilient layer to serve as a bearing surface for the condyle, whether natural or artificial.

Means are provided for attaching the plate to the skull such that the plate is positioned and securely held against the mandibular fossa and articular eminence, with the resilient layer disposed between the two.

A preferred form of the mandibular component comprises a rigid, thin-walled, generally upright channel having a J-shaped cross-section with open upper and lower ends, which is formed of a strong, biocompatible material, preferably cast Vitallium, to slip over and generally conform to the posterior border of a ramus from which the natural condyle has been removed.

An artificial condyle, comprising an anatomically-correct, laterally elongated and tapered head disposed above a narrowed neck and shoulders, is molded onto the upper end of the channel from a hard, smooth, biocompatible plastic material, preferably high density polyethylene or acrylic, such that it fairs smoothly onto, and serves as a closure for, the upper end of the channel.

Means are provided for rigidly securing the channel to the ramus.

A better understanding of the system, as well as the fabrication and use of its components, may be had from a consideration of the following description of some exemplary preferred embodiments thereof, particularly when read in conjunction with the appended drawings, in which:

DETAILED DESCRIPTION OF THE DRAWINGS

FIG. 1 is a right lateral view of a metallic articular eminence implant of the prior art illustrated in place within the TMJ of a human skull, shown in phantomed lines;

FIG. 2 is a plan view of the prior art implant shown in FIG. 1;

FIG. 3 is a right lateral view of a glenoid fossa implant in accordance with the present invention;

FIG. 4 is a sectional view into the fossa implant of FIG. 3, as revealed by the section taken therein along the line 4—4;

FIG. 5 is a right lateral view of the total TMJ replacement prostheses of the present invention showing the glenoid fossa component illustrated in FIGS. 3 and 4 used in conjunction with the condylar component of the present invention;

FIG. 6 is a sectional view into the condylar implant illustrated in FIG. 5, as revealed by the section 6—6 taken therein; and FIG. 7 is another sectional view into the condylar implant shown in FIG. 5, as revealed by the section 7—7 taken therein.

DESCRIPTION OF THE PREFERRED EMBODIMENTS

As illustrated in FIG. a temporomandibular joint 1 comprises a skull's glenoid fossa region, which includes the temporal bone 2 on the posterior border, the articular eminence portion 3 of the zygomatic arch 4 on the anterior border, and the concave, arcuate mandibular fossa region 5 between the two. An oblate, laterally elongated and tapered condyle 6 is disposed atop the ramus portion 7 of the mandible or jaw 8 and resides within the glenoid fossa to move anteriorly and inferiorly in a rolling, sliding movement over the eminence with jaw opening. Not illustrated in the figures are the other important soft structures of the joint, which include the mandibular disc, muscle attachments, and the capsular ligament.

An artificial articular eminence 9 of a type described in some detail in U.S. Pat. No. 3,579,643 is illustrated in a right lateral view in FIG. 1, and in a planar view in FIG. 2. This prior art prosthesis comprises a thin (1/64"), metallic plate anatomically contoured to overlay only the articular eminence portion 3 of the mandibular joint.

The artificial eminence 9 includes a superior surface 10 which resides close up against the inferior surface of the natural eminence 3, and is positioned and held in place by means of a superiorly-extending zygomatic flange 11, which is secured to the zygion 4 by means of screws (not illustrated) extending through apertures 12 contained in the flange.

One of the problems associated with such prior art temporal implants is the difficulty in achieving an acceptable anatomical fit in the region of the mandibular fossa 5, especially when coupled with the necessity of maintaining a desired spacing below the skull of the "floor" of an artificial mandibular fossa. This may be because there has been loss of bone at either the fossa, the condyle 6, or both. In such cases, a large number of such rigid implants of various sizes must be made available during the surgical procedure so that the one closest to that having the appropriate fit and vertical floor dimension may be quickly selected.

Because of this drawback, some have suggested the use of glenoid fossa implants of more flexible and resilient materials, e.g., silicone rubber. However, as explained above, such materials can creep and deform over time with a resultant loss in dimensional stability. More undesirably, their coaction with the condyle 6, whether natural or artificial, can slough off particles of the material, which in turn, may cause foreign body giant cell reaction with the surrounding tissue.

I have discovered that a mandibular fossa implant 50 of the type illustrated in FIG. 3 and discussed in more detail hereinafter eliminates the foregoing problems of the prior art prostheses while still retaining the advantages of both the rigid metallic prostheses and those incorporating more resilient materials.

The preferred mandibular fossa implant 50 illustrated comprises a thin, rigid plate 52 of biologically inert material which is contoured to generally conform to and overlay at least the articular eminence and mandibular fossa portions of the glenoid fossa. I have found that, depending upon the particular application, the plate 52 can be fabricated from a variety of materials, provided that they are strong, rigid, biocompatible, and provide a smooth, non-galling surface for the condyle to slide upon. These materials include such metals as tantalum, stainless steel, and most preferably, the chrome/cobalt alloy known as Vitallium ®.

The plate 52 includes a convex anterior portion 54 which overlays both the descending and ascending portions of the articular eminence, as well as a generally concave posterior portion 56 which extends at least about halfway into the mandibular fossa, but does not cover the petro-tympanic suture. Some of the prior art fossa prostheses, e.g., U.S. Pat. No. 3,178,728, did cover this suture, but there are important structures carrying through this suture or fissure which could be interfered with, if covered. These include the disco-malleolar ligament, the anterior tympanic artery and the chordae tympany nerve.

The plate includes a superior surface 58 which is disposed to face toward the eminence and mandibular fossa, and a smoothly polished inferior surface 60 disposed oppositely thereof to serve as a smooth, hard, bearing surface for the condyle.

In the region of the eminence, the anterior portion 54 is disposed upon the zygion with the superior surface 58 of the plate 52 in touching contact with the zygomatic bone (see FIG. 4). Posteriorly of the eminence, the superior surface 58 of the plate is spaced apart from the floor of the mandibular fossa by means of a conforming layer 62 of flexible, resilient, biocompatible material adhered to the superior surface of the plate and sandwiched between the plate and the floor of the natural fossa.

The implant is rigidized and held securely in position by means of a lateral flange 64 which extends superiorly to conform to and overlay the lateral aspect of the zygoma. The flange 64 includes a plurality of apertures 66 for receiving screws 67 which tap directly into the bone to secure the implant in place.

In the preferred embodiment of the implant 50, the material of the conforming layer 62 consists of a cured silicone rubber, e.g., Silastic ®, which is adhered to the superior surface 58 of the plate with a suitable adhesive. This bilaminar construction provides a number of advantages:

First, as a "spacer", the Silastic layer is easily provided in a variety of thicknesses and can be easily shaved or trimmed at the time of surgery to adjust the plate's vertical position easily and precisely. This means, for example, in the case of a damaged condyle, wherein there is a loss of condylar bone and vertical dimension, perhaps with concurrent occlusal changes, the bone loss can be easily compensated for by lowering the floor of the fossa, thereby obviating the need for a total TMJ replacement in some patients.

Second, the flexibility of the layer 62 permits the relatively rigid plate 52 to conform to the complex architecture of the floor of the natural fossa without the need for a large number of plate sizes, while its resiliency ensures that the hard, smooth inferior bearing surface 60 of the plate will be adequately "backed up" against the mandibular fossa so that the forces imposed by the condyle upon the inferior surface in this region are transmitted uniformly to the remaining temporal portion of the joint without movement of the implant.

Thus, the bilaminar construction of the present invention affords the advantages of both the rigid metallic implants and the resilient implants of the prior art, while avoiding their disadvantages.

Advantageously, the temporal implant component 50 described above may be used independently, or in the case of a total TMJ replacement, in conjunction with the novel condylar, or mandibular implant component 100 of the present invention, which is illustrated in FIGS. 5–7 and described hereinbelow.

The condylar prosthesis 100 comprises a thin-walled, generally upright channel 102 having a J-shaped cross-section (see FIG. 7) with open upper and lower ends 104, 106. The channel 102 is formed or cast from a strong, biocompatible metal alloy, such as tantalum, stainless steel, or preferably, Vitallium, to slip over and conform to the posterior border of a ramus 7 from which the natural condyle has been surgically removed. The shape of the channel provides the implant with a degree of stiffness and strength in the vertical direction which approaches or exceeds that of the mandible itself when the implant is attached.

The lateral sidewall of the channel 102 is provided with a plurality of fastener openings 108 through which number of Vitallium screws 110 extend to tap directly into the ramus, thereby securing the prosthesis 100 firmly to the ramus in the appropriate vertical and horizontal position.

Disposed at the open upper end 104 of the channel 102 is an anatomically correct artificial condyle 112. The condyle 112 is molded from a hard, smooth, biocompatible plastic material to include a laterally elongated and tapered head 114 situated atop a narrowed neck and shoulders portion 116. The latter portion is molded to fair smoothly into, and serves to "close", the upper end of the channel structurally, the plastic material extending down along the sidewalls of the channel both inside and out. This "closure" of the channel further serves to strengthen and rigidize the structure of the implant and to prevent wracking of the channel with stress.

The plastic material of the artificial condyle 112 can be either polyethylene or acrylic, either of which is easily custom molded using conventional techniques. It should be noted that an anatomical condyle made of polyethylene or acrylic can be used alone, i.e., without a temporal component, since the condyle is made of a relatively soft material and anatomically spreads the forces more evenly over the mandibular fossa. However, it is usually better in the long run to have a temporal component such as the temporal implant 50 described above working in conjunction with the condylar component 100.

It will be noted that the exemplary implants 50 and 100 illustrated and discussed herein are, for purposes of discussion and illustration, confined to those adapted for use on the patient's right side. However, as may be expected, those adapted for use on the patient's left side are simply mirror images of their right side counterparts, as reflected through the sagittal plane.

Likewise, skilled practitioners will recognize that the particular embodiments discussed and illustrated herein are exemplary in nature, so that many modifications thereof are possible in terms of materials, construction and application, depending upon the particular problem at hand. Accordingly, the scope of the present invention should be limited only by the claims appended hereinafter.

What is claimed is:

1. A temporomandibular surgical implant, comprising:
   a thin, rigid plate of biologically inert metal contoured to generally conform to and overlay at least the articular eminence and about half of the mandibular fossa portions of the glenoid fossa, but not the petro-tympanic fissure, said plate having a superior surface for disposition facing toward the articular eminence and mandibular fossa, and a smooth, hard, non-wearing, condyle-bearing inferior surface facing away therefrom;
   a layer of resilient, biologically inert, non-metallic material securely attached to, and contacting only, said superior surface of said plate and disposed thereon to reside between said plate and the floor of the mandibular fossa such that minute spaces between said plate and said floor are occupied by said layer, said layer having a thickness which can be quickly reduced by manual trimming or shaving of said layer such that the position of said plate relative to said floor can be finely adjusted contemporaneously with implantation; and
   attachment means for attaching said plate to the skull such that said plate is held in a desired position relative to said mandibular fossa and articular eminence, with said resilient layer sandwiched therebetween.

2. The implant of claim 1 wherein said attachment means further comprises:
   said plate having a lateral portion formed to extend superiorly and conform to and overlay inferior and lateral surfaces of the zygion, said portion containing a plurality of apertures therein; and
   a plurality of screws extending through said apertures and into the skull.

3. The implant of either claim 1 or claim 2, wherein said layer is comprised of a silicone rubber material.

4. The implant of either claim 1 or claim 2, wherein said plate is fabricated from one of the following materials: tantalum, Vitallium ®, or stainless steel.

5. The implant of claim 3, wherein said plate is fabricated from one of the following materials: tantalum, Vitallium ®, or stainless steel.

6. A condylar prosthesis for temporomandibular joint implantation, comprising:
   a thin-walled, generally upright channel fabricated of a strong, biocompatible metal alloy and having a J-shaped horizontal cross-section and open upper and lower ends,
   said upper end of said channel having an anatomically correct, artificial condyle molded from a hard, smooth, non-metallic, biocompatible plastic material attached to it in such a manner that said artificial condyle forms a closure of said open upper end of said channel, thereby reinforcing said channel against torsional and wracking forces applied to it, and whereby said artificial condyle is supported by said channel across a substantial portion of its mediolateral extent,
   said lower end of said channel being shaped to slip over, wrap around, and generally conform to, the posterior border of a natural ramus from which the natural condyle has previously been removed, whereby said artificial condyle can be positioned both vertically and anteroposteriorly relative to said ramus before said channel is secured thereto; and
   means for rigidly securing said channel to the ramus.

7. The prosthesis of claim 6, wherein said means for securing said channel to the ramus further comprise said channel having a lateral sidewall containing a plurality of fastener openings therethrough.

8. The prosthesis of either claim 6 or claim 7, wherein said artificial condyle is comprised of acrylic or polyethylene.

9. The prosthesis of either claim 6 or claim 7, wherein said channel is formed from one of the following materials: tantalum, Vitallium ® or stainless steel.

10. The prosthesis of claim 8, wherein said channel is formed from one of the following materials: tantalum, Vitallium ® or stainless steel.

11. A total temporomandibular joint replacement system, comprising:
   a temporal component, comprising:
      a thin, rigid plate of biologically inert metal contoured to generally conform to and overlay at least the articular eminence and about half of the mandibular fossa portions of the glenoid fossa, but not the petro-tympanic fissure, said plate having a superior surface for disposition facing toward the articular eminence and mandibular fossa, and a smooth, hard, non-wearing, condyle-bearing inferior surface facing away therefrom;
      a layer of resilient, biologically inert, non-metallic material securely attached to, and contacting only, said superior surface of said plate and disposed thereon to reside between said plate and the floor of the mandibular fossa such that minute spaces between said plate and said floor are occupied by said layer, said layer having a thickness which can be quickly reduced by manual trimming or shaving of said layer such that the position of said plate relative to said floor can be finely adjusted contemporaneously with implantation; and a mandibular component, comprising:

a thin-walled, generally upright channel fabricated of a strong, biocompatible metal alloy and having a J-shaped horizontal cross-section and open upper and lower ends, said upper end of said channel having an anatomically correct, artificial condyle molded from a hard, smooth, non-metallic, biocompatible plastic material attached to it in such a manner that said artificial condyle forms a closure of said open upper end of said channel, thereby reinforcing said channel against torsional and wracking forces applied to it, and whereby said artificial condyle is supported by said channel across a substantial portion of its mediolateral extent, said lower end of said channel being shaped to slip over, wrap around, and generally conform to, the posterior border of a natural ramus from which the natural condyle has previously been removed, whereby said artificial condyle can be positioned both vertically and anteroposteriorly relative to said ramus before said channel is secured thereto.

12. The joint replacement system of claim 11, wherein said plate is formed from one of the following materials: tantalum, Vitallium ®, or stainless steel.

13. The joint replacement system of either claim 11 or claim 12, wherein said layer is comprised of Silastic ®.

14. The joint replacement system of either claim 11 or claim 12, wherein said channel is formed from one of the following materials: tantalum, Vitallium ® or stainless steel.

15. The joint replacement system of claim 13, wherein said channel is formed from one of the following materials: tantalum, Vitallium ®, or stainless steel.

16. The joint replacement system of either claim 11 or claim 12, wherein said artificial condyle is comprised of acrylic or polyethylene.

17. The joint replacement system of claim 13, wherein said artificial condyle is comprised of acrylic or polyethylene.

18. The joint replacement system of claim 14, wherein said artificial condyle is comprised of acrylic or polyethylene.

19. The joint replacement system of claim 15, wherein said artificial condyle is comprised of acrylic or polyethylene.

* * * * *